(12) United States Patent
Quillin

(10) Patent No.: US 8,389,535 B2
(45) Date of Patent: Mar. 5, 2013

(54) L-METHYLFOLATE TREATMENT FOR PSYCHIATRIC OR NEUROLOGIC DISORDERS

(76) Inventor: Robert L. Quillin, League City, TX (US)

( * ) Notice: Subject to any disclaimer, the term of this patent is extended or adjusted under 35 U.S.C. 154(b) by 0 days.

(21) Appl. No.: 13/237,373

(22) Filed: Sep. 20, 2011

(65) Prior Publication Data

US 2012/0010210 A1    Jan. 12, 2012

Related U.S. Application Data

(62) Division of application No. 12/803,643, filed on Jul. 1, 2010.

(51) Int. Cl.
*A61K 31/505* (2006.01)
*A61F 9/02* (2006.01)

(52) U.S. Cl. .................................. 514/269; 424/436

(58) Field of Classification Search .................. None
See application file for complete search history.

(56) References Cited

U.S. PATENT DOCUMENTS

2006/0160104 A1 * 7/2006 Johnson et al. ................. 435/6

FOREIGN PATENT DOCUMENTS

WO    WO 2006/119589 A2    11/2006
WO    WO 2006119589 A2 *  11/2006

OTHER PUBLICATIONS

Barkley et al., Side Effects of Metlyiphenidate in Children With Attention Deficit Hyperactivity Disorder: A Systemic, Placebo-Controlled Evaluation, Pediatrics, vol. 86, No. 2, Aug. 1, 1990 (Abstract).*

Moretti et al., "Cerebral Folate Deficiency with Developmental Delay, Autism, and Response to Folinic Acid," Neurology, 64, 1088-1090 (2005).

Boris et al., "Association of MTHFR Gene Variants with Autism," Journal of American Physicians and Surgeons, 9(4): 106-109 (2004).

Applicant's co-pending parent U.S. Appl. No. 12/803,643, filed Jul. 1, 2010.

PCT International Searching Authority/US, International Search Report, mailed Oct. 6, 2011, for PCT/US2011/39700, "L-Methylfolate Treatment for Psychiatric or Neurologic Disorders."

PCT International Searching Authority/US, Written Opinion of the International Searching Authority, mailed Oct. 6, 2011, for PCT/US2011/39700, "L-Methylfolate Treatment for Psychiatric or Neurologic Disorders."

* cited by examiner

*Primary Examiner* — Sreeni Padmanabhan
*Assistant Examiner* — Svetlana M Ivanova
(74) *Attorney, Agent, or Firm* — Jones Walker

(57) ABSTRACT

Provided herein are methods of treating neuropsychiatric disorders or improving the symptoms associated therewith administering a medical food, such as L-methylfolate, to a subject having the disorder. The neuropsychiatric disorder may be an autism spectrum disorder or attention deficit disorder with or without hyperactivity (ADD/ADHD). The L-methylfolate may be administered as an adjunct to other therapeutic agents effective to treat the disorder. The subject preferably may be a child and also may have a single nucleotide polymorphism in the MTHFR gene associated with reduced expression of MTHFR enzyme. Also provided is a method of increasing the de novo synthesis of neurotransmitters in vivo by transporting a methyl-donating compound across the blood-brain barrier in a subject.

15 Claims, No Drawings

L-METHYLFOLATE TREATMENT FOR PSYCHIATRIC OR NEUROLOGIC DISORDERS

CROSS-REFERENCE TO RELATED APPLICATIONS

This application is a division of and claims priority to U.S. application Ser. No. 12/803,643, filed Jul. 1, 2010.

BACKGROUND OF THE INVENTION

1. Field of the invention

The present invention relates to the fields of neuropsychiatry and medical foods. More specifically, the present invention relates to methods for increasing de novo synthesis of neurotransmitters in vivo and treating neuropsychiatric and/or neurologic disorders, such as autism spectrum disorders and attention deficit disorder with or without hyperactivity, with the medical food L-methylfolate.

2. Description of the Related Art

The number of cases of autism spectrum disorders (ASDs), as of 2010, was estimated at 307,749 with a U.S. annual economic cost of over 9 billion dollars (www.fightingautism.com). The number of cases has increased from 15,580 in 1992 to 292,818 in 2008 for children ages 6 to 22 years old, or 337,795 if all children are included starting at 3 years old versus starting at 6 years old. This represents a cumulative growth in the number of cases of autism of 1779% (www.cdc.gov). Suggested etiologies for the increase in autism rates include: the increased attention received diagnostically, the influence of environmental factors, and finally the overall influence of genetics and susceptibility (1-4).

Attention deficit disorder with and without hyperactivity (ADD/ADHD) is considered by some to be closely related to the spectrum of autism (5-6). As of 2006, 4.5 million children, ages 5-17 years, have ever been diagnosed with ADD/ADHD. Three to seven percent of school age children suffer from ADHD. The diagnosis of ADHD has increased an average of 3% per year from 1997-2006. And, the cost of the illness (using a 5% prevalence rate) is estimated to be between $36 and $52 billion (7). The exact causes of ADD/ADHD, like autism spectrum disorders, are not known. Evaluation of the genetics, environmental factors, and level of diagnostic attention also suggests multifactorial causes similar to autism spectrum disorders (8-10).

Despite the prevalence of autism spectrum disorders and attention deficit disorders, research to this point has not revealed consensual or conclusive etiologies to direct more effective and consistent treatment modalities. To better address effective treatment regimens, it may be necessary to revisit the suspected mechanisms of illness. This would best be done by evaluating the biochemical pathology of these illnesses, specifically evaluating the role of neurotransmitters.

Dopamine, norepinephrine, and serotonin are neurotransmitters critical to maintaining basic neurological and psychological balance in the human brain. Dopamine and norepinephrine are essential to maintaining alertness, attention, impulse control and executive functions. Serotonin is directed toward the control of appetite, sleep, memory and learning, temperature regulation, and mood and behavior. The clinical symptoms associated with ADHD and autism spectrum disorders reflect the imbalance in these neurotransmitters, not alone, but in conjunction with each other.

Medications currently used in the treatment of ADHD and autism spectrum disorders function to maintain this neurotransmitter balance. Dopamine and norepinephrine are prevented from uptake through various formulations of stimulants; serotonin, by selective serotonin reuptake inhibitors (SSRIs). In the case of ADHD, a deficiency of dopamine and norepinephrine is implicated. In autism, the deficiency likely involves all neurotransmitters, but primarily serotonin. The primary dilemma in clinical medicine is how to treat these conditions on the wide spectrum in which they exist.

In order to better treat the symptoms of this broad spectrum of neuropsychiatric disorders, it would be beneficial to identify a common point of therapy. One such point may be found in the enzyme methylenetetrahydrofolate reductase (MTHFR). Methylenetetrahydrofolate reductase is critical for the conversion of dietary folate to L-methylfolate. L-methylfolate is the active form of folate used in the brain for the formation of neurotransmitters. This enzyme is, in turn, encoded by the methylenetetrahydrofolate reductase gene for which exist multiple gene forms or polymorphisms.

In studies looking at the function of methylenetetrahydrofolate reductase polymorphisms, mutations have been implicated to encode this critical enzyme in a deficient manner (11). The deficient or reduced activity of methylenetetrahydrofolate reductase results in lower levels of L-methylfolate in the brain. A critical relationship exists between folate metabolism and methionine biosynthesis at the intersection point of the functional methylenetetrahydrofolate reductase enzyme. This junction in folate metabolism is critical for proceeding to the production of single methyl groups in methionine biosynthesis for DNA and downstream onto neurotransmitter synthesis.

In a normal functioning folate pathway, this transfer of methyl groups occurs via an irreversible reduction of 5,10-MTHF to L-methylfolate. The methyl trap, a commonly accepted hypothesis in biochemistry, also refers to this critical step in folate metabolism and supports an irreversibility that occurs by design. In vitamin B12 deficiency or related conditions, e.g. pernicious anemia, L-methylfolate accumulates due to an inability to transfer the methyl group to homocysteine by the B12 coenzyme-dependent transferase. The methyl groups are "trapped" as L-methylfolate in this condition. And, this critical step is unable to proceed due to lack of vitamin B12 and unable to reverse the pathway because of the irreversible reduction. Research reveals an abnormal "reversibility" that may occur at this critical step as a result of this dysfunctional or polymorphic form of the methylenetetrahydrofolate reductase enzyme.

A study by Goin-Kochel et al. analyzed a population of 147 children with autism spectrum disorders and methylenetetrahydrofolate reductase polymorphisms. The data on the children were taken from the Autism Genetic Resource Exchange (ACRE) and met strict criteria for autism, and the children had been evaluated for the methylenetetrahydrofolate reductase 677C>T polymorphism. Additionally, the study examined the use of vitamins/supplements including folate, but given the limited use of the supplements in the study population it was not believed that the supplementation would alter the data analysis. This study helps to clarify the genetic association of the methylenetetrahydrofolate reductase polymorphisms with autism spectrum disorders (12).

In evaluating the study population for the hypothesized deficiency in CSF folate, the primary limitation in determining potential response to folate is the lack of available serum analysis which could reflect a CSF deficit. James et al reported on methionine cycle and transsulfuration metabolites when evaluating 20 autistic children and their controls. The results revealed significant differences between case and control, but values were not out of the accepted normal range for the same values. Folate metabolites were not measured specifically (13). Another study by Moore, et al has demonstrated the clinically significant differences between interstitial fluids of muscle when compared to serum values for the same metabolites. It is hypothesized that the elusiveness to the etiology and treatment of autism spectrum disorders and ADHD may be attributed to similar discrepancies when comparing serum and CSF measures of folate and its metabolites and significant cofactors including vitamin B12.

Commercial use of L-methylfolate as an approach to folate supplementation has been used in prenatal care because, for example, low folate status may be involved in neural tube defects, pregnancy miscarriage, low fetal birth weight and age-related high risk complications of pregnancy, homocysteine management, and the treatment of depression, dementia and cardiovascular diabetic neuropathy conditions. L-methylfolate has been developed and are marketed under the brand names Metafolin®, Cerefolin NAC®, Deplin®, Metanx®, Neevo® and Zervalx®.

In the absence of treatment modalities for MTHFR polymorphisms or pathologies arising from other downstream defects in folate metabolism with or without the presence of an MTHFR polymorphism being present, unique approaches to the treatment of associated neuropsychiatric disorders are needed. Thus, a recognized need is still present in the art for effective therapeutic methods to alleviate or treat neuropsychiatric disorders, such as, but not limited to, autism spectrum disorders and attention deficit disorders. The present invention fulfils this longstanding need in the art.

SUMMARY OF THE INVENTION

The present invention describes the use of L-methylfolate in children with Asperger's syndrome, autism, pervasive developmental disorder NOS, ADD/ADHD which shows promise as evidenced by improved social interaction and decrease psychomotor agitation.

The present invention is directed to a method for increasing in vivo de novo synthesis of neurotransmitters associated with the folate cycle. The method comprises transporting across a blood brain barrier a compound effective to provide methyl groups for methionine biosynthesis and concurrent de novo synthesis of the neurotransmitters. Representative neurotransmitters whose synthesis may be increased include but are not limited to dopamine, norepinephrine or serotonin.

The present invention also is directed to a method for treating a psychiatric and/or neurologic disorder in a subject. This method comprises administering a pharmacological amount of a compound effective to supplement a folate deficiency in the subject thereby treating the psychiatric and/or neurologic disorder. In a related invention, the method further comprises administering one or more other agents effective to treat the psychiatric and/or neurologic disorder.

The present invention is directed further to a method for improving behavioral or neurological symptoms associated with autism spectrum disorders or related psychiatric and/or neurologic disorders in a subject. This method comprises administering to the subject a dose of L-methylfolate that is increased as the behavioral or neurological symptoms associated with the disorder decrease thereby improving the symptoms associated with the autism spectrum disorders or related disorders. In a related invention, the method further comprises administering one or more other agents effective to treat the psychiatric and/or neurologic disorders.

Other and further aspects, features, benefits, and advantages of the present invention will be apparent from the following description of the presently preferred embodiments of the invention given for the purpose of disclosure.

DETAILED DESCRIPTION OF THE INVENTION

As used herein, the term "a" or "an" when used in conjunction with the term "comprising" in the claims and/or the specification may mean "one," but it is also consistent with the meaning of "one or more," "at least one," and "one or more than one."

As used herein, the term "or" in the claims is used to mean "and/or" unless explicitly indicated to refer to alternatives only or the alternatives are mutually exclusive, although the disclosure supports a definition that refers to only alternatives and "and/or."

As used herein "L-methylfolate" refers to the natural, active form of folate or 6(S)-5-methyltetrahydrofolate (6(S)-5-MTHF) used, inter alia, at the cellular level for DNA reproduction, the cysteine cycle and the regulation of homocysteine among other functions. L-methylfolate also refers to a formulation or pharmaceutical formulation or medical food for oral administration or ingestion to a subject, preferably to a child, for the treatment of psychiatric and/or neurologic disorders. L-methyl folate is available commercially in formulations such as, but not limited to, Metafolin®, Cerefolin NAC®, Deplin®, Metanx®, Neevo® and Zervalx®.

As used herein, the terms "MTHFR gene" or "MTHFR polymorphism" refer to the gene encoding the enzyme methylenetetrahydrofolate reductase or to one of 24 single amino acid mutations, for example, the C677T mutation, therein, respectively.

As used herein, the term "subject" refers to the recipient, such as a child or an adolescent or an adult, of an oral formulation or dosage of L-methylfolate.

In one embodiment of the present invention, there is provided a method of increasing in vivo de novo synthesis of neurotransmitters associated with the folate cycle, comprising transporting across a blood brain barrier a compound effective to donate methyl groups for methionine biosynthesis and concurrent de novo synthesis of the neurotransmitters.

In this embodiment, oral administration of the compound effects transport across the blood brain barrier. An example of a methyl-donating compound is L-methylfolate or a pharmacological salt or hydrate thereof. In this embodiment, representative neurotransmitters are one or more of dopamine, norepinephrine or serotonin.

The L-methylfolate may be administered to a subject diagnosed with an autism spectrum disorder or attention deficit disorder with or without hyperactivity. In addition, the subject may have a single nucleotide polymorphism in the MTHFR gene. Furthermore, the L-methylfolate may be administered at an initial dose of about 2.5 mg to about 15 mg as would be known by a person having ordinary skill in this art. Further still, the dose may be increased during a period of about 7 days to about 30 days from initial administration.

In another embodiment of the present invention there is provided a method for treating one or both of a psychiatric or neurologic disorder in a subject, comprising administering a pharmacological amount of a compound effective to supplement one or both of a serum or suspected cerebrospinal folate deficiency in the subject thereby treating the psychiatric and/or neurologic disorder. Further to this embodiment, the method comprises administering one or more other agents effective to treat the psychiatric and/or neurologic disorder disorder. In this further embodiment the other agent(s) may be administered concurrently or consecutively with the compound.

In both embodiments, the compound may be a medical food. Particularly, the medical food may be L-methylfolate or a pharmacological salt or hydrate thereof. A dose of the compound may be a daily dose of about 2.5 mg to about 15 mg or a dose determined by one having ordinary skill in the art based on the medical circumstances of a particular patient. Furthermore, the dose may be escalated during a period of about 7 days to about 30 days from initial administration.

Furthermore, in both embodiments the neuropsychiatric disorder may be an autism spectrum disorder, attention deficit disorder with or without hyperactivity or a combined subtype thereof. Comorbid disorders are commonly associated with the above mentioned conditions, including but not limited to, learning disorders, speech disorders, mental retardation, and comorbid anxiety with or without oppositional or conduct disorders. The subject also may have a nucleotide polymorphism in the MTHFR gene associated with reduced expression of MTHFR enzyme. The subject may be a child.

In yet another embodiment of the present invention, there is provided a method for improving behavioral or neurological symptoms associated with autism spectrum disorders or one or both of related psychiatric or neurologic disorders in a subject, comprising administering to the subject a dose of L-methylfolate that is increased as the behavioral or neurological symptoms associated with the disorder decrease thereby improving the symptoms associated with the autism spectrum disorders or related disorders.

Further to this embodiment the method may comprise administering one or more other agents effective to treat the psychiatric and/or neurologic disorder as described supra. The initial administered dose may be administered in those amounts and increased after initial administration as described supra. In addition, representative related psychiatric and/or neurologic disorders include but are not limited to attention deficit disorder with or without hyperactivity. Furthermore, the subject may have the MTHFR gene polymorphism as described. A representative subject includes but is not limited to a child.

The present invention provides methods of treating psychiatric and/or neurologic disorders with a medical food, such as L-methylfolate. Particularly, L-methylfolate is useful as a monotherapeutic or as an adjunct for the treatment of the neuropsychiatric disorders in a subject. However, it is contemplated that L-methylfolate may obviate the need for other medications in a subset of subjects. Also, L-methylfolate treatment has demonstrated efficacy in both the presence and in the absence of MTHFR polymorphisms.

The subject has a neuropsychiatric disorder such as, but not limited to, an autism spectrum disorder or an attention deficit disorder with or without hyperactivity as defined by Diagnostic and Statistical Manual of Mental Disorders (DSMIV). The subject may be any individual, but, preferably, the subject is a child. Clinical response to treatment is identified with respect to changes in behaviors associated with or symptomatic of the disorder verses changes in actual measureable metabolites before or after the administration of L-methylfolate.

Formulations of L-methylfolate, such as pharmaceutical hydrates or salts, are well-known in the art and commercially available. They may comprise, for example, tablet, capsule, powder or liquid forms. It is well-known and standard that such formulations may further comprise excipients or carriers, or other inert or preservative ingredients, etc. One of ordinary skill in the art is well-suited to determine a formulation appropriate to a subject's age, health or general condition. It is also contemplated that pharmacologically acceptable derivatives or analogs of L-methylfolate may be used to effect improvement.

The L-methylfolate may be administered daily in a single oral dose or in any form or fashion as would be readily recognizable to one having ordinary skill in this art. Dose is weight dependent and may range from 2.5 mg to 15 mg as shown in Example 1. Dose may be increased over a period that is about 7 to about 30 days from the initial oral administration. Increases in dose are dependent upon a demonstrable improvement in behaviors or conditions associated with the psychiatric and/or neurologic disorder.

L-methylfolate may be administered as an adjunct to other known therapeutic agents or drugs or pharmaceutical compositions thereof effective to treat the psychiatric and/or neurologic disorder. One of ordinary skill in the art is well able to determine which, if any, agent or drug is a suitable choice for the subject. Such determination would depend upon the particular psychiatric and/or neurologic disorder, the severity or stage of the psychiatric and/or neurologic disorder, other drugs currently taken by the subject, the subject's age, general health, etc.

As a medical food or other suitable formulation, L-methylfolate crosses the blood brain barrier. L-methylfolate is incorporated into the folate cycle at a critical step while bypassing the deficient MTHFR enzyme. Thus, the present invention also provides a method for the in vivo de novo synthesis of neurotransmitters, for example, dopamine, norepinephrine, and serotonin, associated with the psychiatric and/or neurologic disorders, for example, autism spectrum disorder and ADD/ADHD. A medical food, such as L-methylfolate, is utilized to provide methyl groups for methionine synthesis and concurrent downstream synthesis of neurotransmitters.

The following examples are given for the purpose of illustrating various embodiments of the invention and are not meant to limit the present invention in any fashion.

EXAMPLE 1

Clinical Studies
Inclusion Criteria

Both genders are eligible for study: Healthy volunteers are not accepted. All study participants (parents and legally responsible parties) are given the appropriate privacy statements as required by the Health Insurance Portability and Accountability Act of 1996 (HIPAA). The following inclusion criteria are in place:

1. Child has a confirmed diagnosis of one of the autism spectrum disorders, including but not limited to Asperger's syndrome, or attention deficit disorders (with or without hyperactivity) according to the Diagnostic and Statistical Manual of Mental Disorders (DSMIV).

2. Child is in stable condition with relatively good control of significant medical problems, including liver, kidney, or heart problems, at the time of treatment.

3. Child and parent/legally responsible parties are willing to comply with the proposed treatments after appropriate consent to treat is given. The parent/legally responsible party will attend a presentation regarding the rationale for the study to address any questions or concerns. At the end of the presentation, the parent/legally responsible party will receive a packet to review along with an informed consent. The parent will then be responsible for scheduling the study examination for the child. All appropriate documentation, including informed consent, will be completed prior to the exam and the initiation of therapy.

4. Child is able to take medication, in oral form prepared as tablet, capsule, powder or liquid, as appropriate for age and/or condition.

5. Parent/legally responsible parties agree to provide behavioral data on participating children as outlined in protocol and agrees to being contacted any time during the treatment period.

Exclusion Criteria

The following exclusion criteria are in place:

1. Child is currently being treated for a serious acute illness.
2. Child has a history of acute or chronic liver or renal disease.
3. Child is currently being evaluated for comorbid neurologic or seizure disorder.
4. Child has an allergic reaction to folate or derivatives.
5. Child must not be currently taking supplements or medications considered to interfere with study drug, excluding stimulants. The patient must be weaned off SSRI's or other mood stabilizers prior to implementing treatment.
6. Family does not have capacity to evaluate child.

Candidate Screening

Candidates receive the following tests during screening:

1. Physical exam, inclusive of vital signs/
2. DSMIV criteria as indicated for inclusion criteria.
3. Autism spectrum disorder or ADD screen as appropriate at baseline, 2 weeks, 30 days, and 90 days.
4. Baseline laboratory tests for CBC, serum folate, RBC folate, B12, and homocysteine
5. 30 day labs: As indicated by DSMIV criteria, with MTHFR polymorphism analysis added
6. 90 day labs: As indicated by DSMIV criteria.

EXAMPLE 2

Treatment

Drug Interactions

L-methylfolate is water soluble and rapidly excreted via the kidneys. L-methylfolate does not affect CP-450 system. Potentially, high dose folate may lower the serum level of first generation anticonvulsants and pyrimethamine. Other than an anecdotal report of worsening of behavior symptoms in a patient when folinic acid was increased to 1 mg/kg/d, there are no indications of other side effects when using various forms of folate and its metabolites, including folate and folinic acid.

Particularly, no significant risks have been associated with the use of folate or its metabolites, except to mask pernicious anemia due to lack of vitamin B12. Folic acid, when administered above 800 mcg, may increase the amount of unmetabolized folic acid, which has been linked to accelerated growth of existing neoplasms in the colon. Allergic reactions have been documented with the use of oral and parenteral folate as well as oral L-methylfolate. Patients are provided with the prescription insert.

Contraindications would primarily involve concurrent use of other medications. Antiepileptic drugs, trimethoprim, non-steroidal anti-inflammatory drugs, oral contraceptives, and methylprednisolone may be affected by or affect the metabolism of folate. Other medications can interact with folate, as would be indicated in the prescription insert, but are less likely to be encountered in the pediatric population.

Administration of L-Methylfolate

The patient is dosed with L-methylfolate orally once a day according to preparations available. The patient takes the medication at the same time of day and with a snack or meal. The patient is initially dosed with L-methylfolate according to weight as follows:

25-45 lbs (11-20 kg): 2.5 mg
46-60 lbs (21-27 kg): 5 mg
61-90 lbs (28-41 kg): 7.5 mg
91+ lbs (42+kg): 7.5-15 mg Dose Modifications and Duration of Therapy L-methylfolate is administered in doses and forms appropriate for age. L-methylfolate is titrated upward as indicated by behavior improvement according to the results from the screens. Titration may occur from week 1 through 30 days as indicated by the physician. From 30 days to 90 days, the achieved dose at 30 days is maintained until 90 days to observe for tolerance to drug, side effects. During this time, if the child is not weaned from stimulant medications, attempts are made to lower the stimulant as tolerated and discontinue stimulants if at all possible.

Disruption of Therapy

Given the low side effect profile of the drug, therapy will be discontinued for any of the following reasons:

1. Any adverse event felt to be related to the administration of the drug, including worsening of behavioral or neurological symptoms. Any adverse events as suspected by the parent/legally responsible party will necessitate a phone call, email, or visit with the study physician. Continuation of the therapy, with or without dose adjustment, will be at the request of the parent/legally responsible party and with agreement of the investigator physician. Therapy will only continue if all parties agree that event was not related to the therapy. The adverse event will be recorded in the patient file.
2. Parental concerns or desire to discontinue therapy.
3. Lack of compliance by child or parent/responsible party
4. Child meets any of the exclusion criteria outlined for the study

EXAMPLE 3

Therapy Implementation

In implementing therapy the first consideration is the presence of clinical signs consistent with previous or current diagnosis of an autism spectrum disorder or an attention deficit disorder. Only two patients did not have a history of formalized diagnostic work-up. These patients exhibited symptoms of speech delay, lack of socialization and communication skills, and lack of eye contact. Full evaluation by a developmental pediatrician/geneticist is pending for these two children. The established diagnosis was not a sole indicator for therapy.

Second, a review of the family history is necessary. The information gathered from one or more parents provided additional support for an inherited influence. Parents were questioned about the presence of ADHD or autism spectrum disorders in the immediate family or extended family. Of particular interest was the presence of other neuropsychiatric conditions, such as depression, anxiety, and bipolar disorder. Parents also were queried regarding the presence of heart disease, difficulties with pregnancy due infertility or miscarriages, leukemia, gastric and colon cancers, breast cancer and stroke. In elderly members of the family, the occurrence of dementia, Alzheimer's, and Parkinson's was also discussed. The above diseases have also been associated to varying degrees with the methylenetetrahydrofolate reductase defect.

Third, blood samples were collected and evaluated. The laboratory exams completed on the blood samples were: a complete blood count with differential, serum folate, serum B12, and serum homocysteine. The tests were performed to establish a baseline for red cell morphology while evaluating for any pre-existing pathologies related to anemia, leukemia, or other blood dycrasias. Serum folate and B12 have been implicated in certain pathologies of the red blood cell and are critical components in folate metabolism. Vitamin B12 in the range of 400 pg/ml or less has been associated with neuropsychiatric sequelae in 5-10% of population. (Quest Labs) Finally, elevated homocysteine levels in the serum have been associated with various disease states, particularly in the presence of the methylenetetrahydrofolate reductase gene polymorphisms. It is not clear why homocysteine levels have been found to be lower than normal in the evaluated patient population. However, a few researchers have been able to evaluate severely compromised children. In the examination of the cerebrospinal fluid in these patients, it was discovered that the homocysteine levels were significantly higher when compared to serum findings.

Fourth, serum was evaluated for the presence of methylenetetrahydrofolate reductase polymorphisms as a predictor of condition severity and response to therapy. Given the expense of these analyses, it was decided to delay evaluation of the serum for the polymorphisms until a clinic response was determined. To date only four patients have completed follow up laboratory exams with the methylenetetrahydrofolate reductase analyses. In two of four patients, the test was positive for the presence of the various gene polymorphisms in association with a positive response to therapy. The lack of the methylenetetrahydrofolate reductase gene in the remaining two patients, who have responded to therapy, leaves an associated factor undetermined.

In a preliminary trial, nineteen patients, ages 4-43 years, (3 female, 16 male) were randomly selected over the course of three months. Patients were permitted to remain on current medication or supplemental, i.e., fish oil and vitamins, therapies at parental request. Of 19 patients, five dropped or were placed on hold for various reasons, primarily academic or financial concerns. Of the 14 remaining, all have had a response to therapy as indicated by parents' correspondence and office visits.

Response to therapy, though not formalized, included a trend toward a more stable, verses labile, mood, increased attentiveness, more easily directed, improved sleep hygiene, and overall improved ability to handle daily stressors. Of the 14 patients, two have had intermediate responses based on parental report, 12 have made significant improvements. The time course of initial improvement has been typified as 3-5 days, two weeks, or 4-6 weeks. No side effects have been reported in the preliminary experience.

It is notable that two children who tested negative for the methylenetetrahydrofolate reductase gene polymorphisms were responding clinically to L-methylfolate treatment according to parental reports. It is contemplated, therefore, that therapeutic benefit is obtained from neurotransmitter synthesis only and/or that a defect may be present during methionine synthesis.

The following references are cited herein.
1. Levy S. E., et al, Lancet, 374(9701):1627-38, 2009
2. Jick, H., et al, Pharmacotherapy, 23(12):1524-30, 2003
3. Muhle, R, et al, Pediatrics, 113(5):e472-86, 2004
4. Currenti, S. A., Cell Mol Neurobiol, 30(2):161-71, 2010
5. Sinzig, J., et al, J Atten Disord, 13(2):117-26, 2009
6. Rommelse, N. N., et al, Eur Child Adolesc Psychiatry, 19(3):281-95, 2010
7. Pelham, W. E., et al, J Pediatr Psychol, 32(6):711-27. 2007
8. Steinhausen, H. C., Acta Psychiatr Scand, 120(5):392-9, 2009
9. Ficks, C. A., Curr Psychiatry Rep, Oct;11(5):387-92, 2009
10. Coghill, D, et al, Expert Rev Neurother, 9(10):1547-65, 2009
11. van der Put, N. M., et al, Am J Hum Genet, 62(5):1044-51, 1998
12. Goin-Kochel, R. P., Autism Res, 2(2):98-108, 2009
13. James, S. J., et al, J Clin Nutr, 80(6):1611-7, 2004

Any patents or publications mentioned in this specification are indicative of the levels of those skilled in the art to which the invention pertains. Further, these patents and publications are incorporated by reference herein to the same extent as if each individual publication was specifically and individually incorporated by reference. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method of treating attention deficit disorder with or without hyper-activity in a subject, comprising the steps of:
   (a) administering a daily dose of L-methylfolate or a pharmacological hydrate or salt thereof to the subject from a treatment day 1 to about a treatment day 7, the daily dose being in the range of 5 mg to 15 mg of said L-methylfolate or pharmacological hydrate or salt thereof depending on the weight of the subject;
   (b) increasing the daily dose of L-methylfolate or pharmacological hydrate or salt thereof administered to the subject in response to an observed decrease in behavioral or neurological symptoms associated with the subject's attention deficit disorder, the increase in the daily dose of the L-methylfolate or pharmacological hydrate or salt thereof occurring from about treatment day 7 to about a treatment day 30 and resulting in a daily achieved dose of L-methylfolate or pharmacological hydrate or salt thereof at about treatment day 30.

2. The method, according to claim 1, further comprising the step of:
   (c) administering the daily achieved dose of L-methylfolate or pharmacological hydrate or salt thereof to the subject from about treatment day 30 to about a treatment day 90.

3. The method according to claim 1, wherein the dose of L-methylfolate or pharmacological hydrate or salt thereof administered to the subject in step (a) is selected from the group consisting of:
   (i) if the subject weighs between 46-60 lbs., the dose is 5 mg;
   (ii) if the subject weighs between 61-90 lbs., the dose is 7.5 mg; and
   (iii) if the subject weighs 91 lbs. or more, the dose is 7.5 mg to 15 mg.

4. The method according to claim 1, wherein the L-methylfolate or pharmacological hydrate or salt thereof is administered orally to the subject.

5. The method according to claim 4, wherein the L-methylfolate or pharmacological hydrate or salt thereof is administered in the form of a pharmaceutical composition, the composition comprising a tablet, a capsule, a powder, or a liquid.

6. The method according to claim 5, wherein the tablet, capsule, powder or liquid includes a pharmaceutically acceptable carrier or excipient.

7. The method according to claim 1, wherein the subject has a nucleotide polymorphism in the MTHFR gene associated with reduced expression of MTHFR enzyme.

8. The method according to claim 1, wherein the subject is a child.

9. The method according to claim 8, wherein the child is 5 to 17 years of age.

10. The method according to claim 1, wherein the subject is an adult.

11. The method according to claim 10, wherein the adult is 18 years of age or older.

12. The method according to claim 1, wherein the L-methylfolate or a pharmacological hydrate or salt thereof is administered to the subject as a monotherapeutic.

13. The method according to claim 1, wherein the L-methylfolate or a pharmacological hydrate or salt thereof is administered to the subject as an adjunct together with the administration to the subject of one or more other agents effective in the treatment of the subject's attention deficit disorder.

14. The method according to claim 13, wherein the one or more other agents is administered concurrently or consecutively with the administration of the L-methylfolate or a pharmacological hydrate or salt thereof.

15. The method according to claim 1, wherein the subject is being administered a dose of a stimulant medication to control the subject's attention deficit disorder, the method further comprising the step of:

(c) reducing or eliminating the dose of stimulant medication being administered to the subject during a period from about treatment day 30 to about treatment day 90.

* * * * *